United States Patent [19]

Keogh

[11] Patent Number: 5,928,916
[45] Date of Patent: Jul. 27, 1999

[54] IONIC ATTACHMENT OF BIOMOLECULES WITH A GUANIDINO MOIETY TO MEDICAL DEVICE SURFACES

[75] Inventor: James R. Keogh, Maplewood, Minn.

[73] Assignee: Medtronic, Inc., Minneapolis, Minn.

[21] Appl. No.: 09/010,906

[22] Filed: Jan. 22, 1998

Related U.S. Application Data

[63] Continuation-in-part of application No. 08/635,187, Apr. 25, 1996, Pat. No. 5,821,343, application No. 09/001,994, Dec. 31, 1997, application No. 08/694,535, Aug. 9, 1996, Pat. No. 5,728,420, and application No. 08/984,922, Dec. 4, 1997.

[51] Int. Cl.$^6$ ............... C12N 11/00; G01N 33/543; C07K 1/00; A61K 38/43
[52] U.S. Cl. ............... 435/174; 424/422; 424/94.1; 435/176; 435/177; 435/180; 435/181; 436/518; 436/524; 436/531; 436/532; 530/402; 530/810; 530/811; 530/815; 530/816
[58] Field of Search ............... 435/174, 176, 435/177, 180, 181; 436/518, 524, 531, 532; 530/402, 810, 811, 815, 816; 424/422, 94.1

[56] References Cited

U.S. PATENT DOCUMENTS

| | | | |
|---|---|---|---|
| 3,826,678 | 7/1974 | Hoffman et al. | 117/81 |
| 4,521,564 | 6/1985 | Solomon et al. | 525/54.1 |
| 4,600,652 | 7/1986 | Solomon et al. | 423/423.3 |
| 4,613,665 | 9/1986 | Larm | 536/20 |
| 4,642,242 | 2/1987 | Solomon et al. | 427/2 |
| 4,720,512 | 1/1988 | Hu et al. | 523/112 |
| 4,786,556 | 11/1988 | Hu et al. | 428/412 |
| 5,032,666 | 7/1991 | Hu et al. | 528/70 |
| 5,053,048 | 10/1991 | Pinchuk | 623/1 |
| 5,077,372 | 12/1991 | Hu et al. | 528/70 |
| 5,110,909 | 5/1992 | Dellacherie et al. | 530/385 |
| 5,344,455 | 9/1994 | Keogh et al. | 623/11 |
| 5,362,852 | 11/1994 | Geoghegan | 530/345 |
| 5,429,618 | 7/1995 | Keogh | 604/266 |

OTHER PUBLICATIONS

R.G. Dickinson et al., "A New Sensitive and Specific Test for the Detection of Aldehydes: Formation of 6–Mercapto–3–substituted–s–traizolo[4,3–β]–s–tetrazines", *Chem. Commun.*, 1719–1720 (1970).

K.F. Geoghegan et al., "Site–Directed Conjugation of Non-peptide Groups to Peptides and Proteins via Periodate Oxidation of a 2–Amino Alcohol. Application to Modification at N–Terminal Serine", *Bioconjugate Chem.*, 3, 138–146 (1992).

A.S. Hoffman et al., ACovalent Binding of Biomolecules to Radiation–Grafted Hydrogels on Inert Polymer Surfaces, @*Trans. Am. Soc. Artif. Intern. Organs*, 18, 10–18 (1972).

S. Holmes et al., AAmination of Ultra–high Strength Polyethylene using Ammonia Plasma, @*Composites Science and Technology*, 38, 1–21 (1990).

Y. Ito et al., AMaterials for Enhancing Cell Adhesion by Immobilization of Cell–Adhesive Peptide,@*J. Biomed. Mat. Res.*, 25, 1325–1337 (1991).

P.H. O=Farrell, AHigh Resolution Two–Dimensional Electrophoresis of Proteins,@*J. Biol. Chem.*, 250, 4007–4021 (1975).

*Primary Examiner*—David M. Naff
*Attorney, Agent, or Firm*—Thomas F. Woods; Harold R. Patton

[57] ABSTRACT

Methods are provided for forming a coating of an immobilized biomolecule on a surface of a medical device to impart improved biocompatibility for contacting tissue and bodily fluids. A biomolecule having a negatively charged moiety is combined with a medical device surface having a positively charged guanidino moiety to form an ionic bond immobilizing a coating of the biomolecule on the surface. In another method, the medical device surface contains an amine moiety that is combined with a guanidino forming agent to form a positively charged guanidino moiety that is combined with the negatively charged moiety to form the ionic bond. In a further embodiment, the medical device surface contains a negatively charged moiety, and a biomolecule containing an amine moiety is combined with a guanidino forming agent to form a positively charged guanidino moiety that is combined with the negatively charged moiety to form the ionic bond.

29 Claims, No Drawings

IONIC ATTACHMENT OF BIOMOLECULES WITH A GUANIDINO MOIETY TO MEDICAL DEVICE SURFACES

CROSS-REFERENCE TO RELATED APPLICATIONS

This application is a continuation-in-part of each applications Ser. Nos. 08/635,187, filed Apr. 25, 1996, now U.S. Pat. No. 5,821,343; 09/001,994, filed Dec. 31, 1997; 08/694,535, filed Aug. 9, 1996, now U.S. Pat. No. 5,728,420; and 08/984,922, filed Dec. 4, 1997. All the foregoing patent applications are hereby incorporated by reference herein, each in its respective entirety. Additionally, application Ser. No. 09/012,056, filed Jan. 22, 1998, is hereby incorporated herein its entirety.

BACKGROUND OF THE INVENTION

For many years, a number of medical devices (e.g., pacemakers, vascular grafts, stents, heart valves, etc.) that contact bodily tissue or fluids of living persons or animals have been developed, manufactured and used clinically. A major problem with such articles is that their surfaces tend to adsorb a layer of proteins from tissues and fluids such as tears, urine, lymph fluid, blood, blood products, and other fluids and solids derived from blood. The composition and organization of this adsorbed protein layer is thought to influence, if not control, further biological reactions. Adverse biological reactions such as thrombosis and inflammation may diminish the useful lifetime of many devices.

Implantable medical devices may serve as foci for infection of the body by a number of bacterial species. Such device-associated infections are promoted by the tendency of these organisms to adhere to and colonize the surface of the device. Consequently, it has been of great interest to physicians and the medical industry to develop surfaces that are less prone to promote the adverse biological reactions that typically accompany the implantation of a medical device.

One approach for minimizing undesirable biological reactions associated with medical devices is to attach various biomolecules to their surfaces. Biomolecules such as antithrombogenics, antiplatelets, anti-inflammatories, antimicrobials, growth factors, proteins, peptides, and the like have been used to minimize adverse biomaterial-associated reactions.

A number of approaches have been suggested to attach such biomolecules. These approaches generally are covalent attachment techniques or ionic attachment techniques. Covalent attachment techniques typically require the use of coupling agents such as glutaraldehyde, cyanogen bromide, p-benzoquinone, succinic anhydrides, carbodiimides, diisocyanates, ethyl chloroformate, dipyridyl disulphide, epichlorohydrin, azides, among others, which serve as attachment vehicles for coupling of biomolecules to biomaterial surfaces. For example, covalent attachment of biomolecules using water soluble carbodiimides is described by Hoffman et al., "Covalent Binding of Biomolecules to Radiation-Grafted Hydrogels on Inert Polymer Surfaces," Trans. Am. Soc. Artif. Intern. Organs, 18, 10–18 (1972); and Ito et al., "Materials for Enhancing Cell Adhesion by Immobilization of Cell-Adhesive Peptide," J. of Biomed. Mat. Res., 25, 1325–1337 (1991).

Coupling molecules used for covalently attaching biomolecules to surfaces may create undesirable crosslinks between biomolecules, thereby destroying the biological properties of the biomolecule, or they may create bonds amongst surface functional sites, thereby inhibiting attachment. Covalent coupling of a biomolecule to a surface may also destroy the biomolecule's three-dimensional structure, thereby reducing or destroying the biological properties of the attached biomolecule, by altering its chemical composition.

Ionic coupling techniques have an advantage of not altering the chemical composition of the attached biomolecule, thereby reducing the possibility of destroying the biological properties of the attached biomolecule. Ionic coupling of biomolecules also has an advantage of releasing the biomolecule under appropriate conditions. One example of the ionic attachment of a biomolecule to a surface is set forth in U.S. Pat. No. 4,442,133 to Greco et al. In this case, a tridodecyl methylammonium chloride (TDMAC) coating is used to ionically bind an antibiotic agent.

Another type of biomolecule which is often coupled to biomaterial surfaces is heparin. Heparin, an anionic bioactive agent, is of great interest to a number of investigators for the development of non-thrombogenic blood-contact biomaterial surfaces. Heparin, a negatively charged glycosaminoglycan, inhibits blood coagulation primarily by promoting the activity of antithrombin III (ATIII) to block the coagulation enzymes thrombin, factor Xa and, to some extent, factors IXa, XIa and XIIa. Surfaces bearing bound heparin have been shown to have anticoagulant activity, therefore, heparinization tends to be a popular technique for improving the thromboresistance of biomaterials. In fact, surface heparinization through an ionic bond is one of the methods used to improve the blood comparability of a variety of biomaterial surfaces.

The original method of heparinization of surfaces was described by Gott et al., "Heparin Binding On Colloidal Graphite Surfaces", Science, 142, 1297–1298 (1963). They prepared a graphite-benzalkonium-heparin surface and observed good non-thrombogenic characteristics. Others followed, treating materials with quaternary ammonium salts to ionically bind heparin. Improving on Gott's technique, Grode et al., "Nonthrombogenic Materials via a Simple Coating Process", Trans. Amer. Soc. Artif. Intern. Organs, 15, 1–6 (1969), eliminated the need for a graphite coating by using tridodecyl methylammonium chloride (TDMAC). Various other quaternary ammonium salts have also been used such as benzalkonium chloride, cetylpyrrdinium chloride, benzyldimethylstearyammonium chloride, benzylcetyidimethylammonium chloride as set forth in U.S. Pat. No. 5,069,899 to Whitbourne and Mangan.

Glutaraldehyde was even used by some investigators to increase the stability of heparin bound ionically through various ammonium groups. Rather than using a low molecular weight quaternary salt or quaternary amine, many investigators incorporated the quaternizable amine directly onto substrates by copolymerization techniques. In another approach, Barbucci et al., "Surface-Grafted Heparinizable Materials", Polymer, 26, 1349–1352 (1985), grafted tertiary amino polymers of poly(amido-amine) structure onto substrates for ionically coupling heparin. The cationic amino groups are capable of interacting electrostatically with the negatively charged groups present in the heparin molecule. They found that the surface's capacity to retain heparin was directly related to the basicity of the grafted cationic amino groups. The greater the basicity of the surface amino groups on the surface, the greater the capacity of the surface has to retain heparin due to a greater percentage of the surface amino groups being protonated at physiological pH.

Current techniques for immobilization of heparin or other biomolecules by an ionic bond have been achieved by introducing positive charges on the biomaterial surface utilizing quaternary ammonium salts and polymers containing tertiary and quaternary amine groups. The main limit to long-term utilization of medical devices containing biomolecules immobilized by the above methods is the rapid release of the biomolecule with time. Therefore, a technique which may ionically bind anionic biomolecules to surfaces for greater lengths of time is highly desired.

SUMMARY OF THE INVENTION

The present invention provides improved methods for ionically attaching a biomolecule to a substrate surface. More particularly, the present invention provides methods for making a medical device having at least one biomolecule ionically immobilized on a biomaterial surface. One method of the present invention includes combining at least one biomolecule comprising a negatively charged moiety with a material comprising at least one positively charged guanidine moiety ($RNHC(NH)NH_2$) or biguanide moiety ($RNHC(NH)NHC(NH)NH_2$) to form an immobilized biomolecule on a medical device biomaterial surface through an ionic bond. A second method of the present invention includes combining at least one biomolecule comprising a positively charged guanidine moiety or biguanide moiety with a material comprising at least one negatively charged moiety to form an immobilized biomolecule on a medical device biomaterial surface through an ionic bond.

DETAILED DESCRIPTION OF THE INVENTION

As used in the specification and claims hereof, the following terms have the particular meanings and definitions set forth below.

I define the term "guanidino moiety" appearing herein to include guanidine, guanidinium, guanidine derivatives such as ($RNHC(NH)NHR'$), monosubstituted guanidines, monoguanides, biguanides, biguanide derivatives such as ($RNHC(NH)NHC(NH)NHR'$), and the like. In addition, the term "guanidino moiety" appearing herein may mean any one or more of a guanide alone or a combination of different guanides.

I define the term "biomolecule" appearing herein as a material that engages in a biological activity or which is effective in modulating a biological activity such as eliminating, reducing or enhancing various biological reactions that typically accompany the exposure of bodily tissues or fluids to a biomaterial. Biomaterial-associated reactions include thrombosis, tissue death, tumor formation, allergic reaction, foreign-body reaction (rejection), inflammatory reaction, infection and cellular attachment and growth. Biomolecules suitable for use in the present invention comprise a negatively charged moiety or a positively charged guanidino moiety or both a negatively charged moiety and a positively charged guanidino moiety. In addition, the term "biomolecule" appearing herein may mean any one or more of a biomolecule alone or a combination of different biomolecules.

I define the term "biomaterial" appearing herein as a material that is substantially insoluble in body fluids and that is designed and constructed to be placed in or onto the body or to contact fluid of the body. Ideally, a biomaterial will not induce undesirable reactions in the body such as thrombosis, tissue death, tumor formation, allergic reaction, foreign-body reaction (rejection) or inflammatory reaction; will have the physical properties such as strength, elasticity, permeability and flexibility required to function for the intended purpose; may be purified, fabricated and sterilized easily; will substantially maintain its physical properties and function during the time that it remains implanted in or in contact with the body. Biomaterials suitable for use in the present invention comprise a negatively charged moiety, such as a phosphate, a sulphate or a carboxylate, or a positively charged guanidino moiety or both a negatively charged moiety and a positively charged guanidino moiety.

I define the term "medical device" appearing herein as a device having surfaces that contact bodily tissue and/or fluids in the course of their operation, which fluids are subsequently used in patients. This definition includes within its scope, for example, extracorporeal devices for use in surgery such as blood oxygenators, blood pumps, blood sensors, tubing used to carry blood and the like which contact blood which is then returned to the patient. The definition includes within its scope endoprostheses implanted in blood contact in a human or animal body such as vascular grafts, stents, pacemaker leads, heart valves, and the like that are implanted in blood vessels or in the heart. This definition also includes within its scope devices for temporary intravascular use such as catheters, guide wires, and the like which are placed into blood vessels or the heart for purposes of monitoring or repair.

The present invention has the objective of solving a number of problems associated with the use of medical devices. The present invention includes within its scope a method for ionically attaching anionic (negatively charged) biomolecules to biomaterial surfaces comprising guanidino moieties for use in medical devices. The present invention further provides a method for ionically attaching biomolecules comprising a guanidino moiety to anionic biomaterial surfaces for use in medical devices.

Guanidine is the imide of urea, or the amidine of carbamic acid. It is a very strong base with a $pK_a$ of 13.5 in water. The great basicity of guanidine is a result of the stability of the conjugated acid (guanidinium) in water. The positive charge on the guanidinium ion can be spread equally among the three nitrogens by resonance. The guanidinium ion is also quite hydrophilic and is well solvated in aqueous media due to the extensive hydrogen bonding of six potential hydrogen bond donors to the solvent. The partial positive charge of the hydrogen bond donors increases their strength for donation to the negative dipole of water. Crystal structures of simple guanidinium derivatives have revealed several common features. First, the C—N single bond length in an alkyl guanidine is typically shorter than the usual C—N single bond length. Usually, the three C—N bonds in the guanidinium group itself are nearly equal in length with an average of 1.33 A. The three N—C—N bond angles are almost always near 120°.

The guanidinium group's features make it a very attractive moiety for incorporation onto biomaterial surfaces. For example, its high basicity (a $pK_a$ of 13.5 for guanidinium itself) allows it to remain protonated over a much wider range of pH than does the ammonium group. In fact, at physiological pH, all but a small fraction of the guanidine molecules will exist as positively charged species. The guanidinium group's enhanced hydrogen bonding capabilities, typically two linear hydrogen bonds, allow it to form tighter complexes with anions that are capable of hydrogen bonding. In fact, the guanidinium group may form characteristic pairs of zwitterionic hydrogen bonds which provide binding strength by their charge and structural organization by their arrangement. The guanidinium functional group with its hydrogen bonding capabilities and its great basicity make it an ideal functional group for ionically attaching anionic biomolecules to biomaterial surfaces.

Biomaterials of the present invention not containing guanidino moieties on their surface may be modified readily to comprise guanidino moieties through a number of methods well known in the art. For example, biomaterials that comprise amines on their surface may be modified to comprise guanidino moieties by reaction with O-methylisourea or S-methylisothiourea to yield substituted guanidines. In fact, guanidino moieties may be synthesized via reaction of an amine with compounds such as S-ethylthiouronium bromide, S-ethylthiouronium chloride, O-methylisourea, O-methylisouronium sulfate, O-methylisourea hydrogen sulfate, S-methylisothiourea, 2-methyl-1-nitroisourea, aminoiminomethanesulfonic acid, cyanamide, cyanoguanide, dicyandiamide, 3,5-dimethyl-1-guanylpyrazole nitrate and 3,5-dimethyl pyrazole. For example, reaction of amines with O-methylisourea, S-methylisourea, S-ethylthiouronium bromide or S-ethylthiouronium chloride, thereby yielding guanidino moieties, are generally completed after 8 hours at 70 degrees Celsius in a solution of sodium hydroxide (NaOH) at pH 10. Reactions of amines with aminoiminomethanesulfonic acid or cyanamide are generally performed at room temperature. Another example is the reaction of an amine with 2-methyl-1-nitroisourea in water to form a nitroguanidine. The nitro group is then easily removed to form a guanidino moiety by hydrogenolysis.

I define the term "guanidino forming agent" appearing herein to include any chemical agent capable of forming a guanidino moiety upon its reaction with a non-guanidino moiety. Examples of guanidino forming agents include S-ethylthiouronium bromide, S-ethylthiouronium chloride, O-methylisourea, O-methylisouronium sulfate, O-methylisourea hydrogen sulfate, S-methylisothiourea, 2-methyl-1-nitroisourea, aminoiminomethanesulfonic acid, cyanamide, cyanoguanide, dicyandiamide, 3,5-dimethyl-1-guanylpyrazole nitrate and 3,5-dimethyl pyrazole. In addition, the term "guanidino forming agent" appearing herein may mean any one or more of a guanidino forming agent or a combination of different guanidino forming agents.

Biomaterials of the present invention not containing amines on their surface may be aminated readily through a number of methods well known in the art. For example, amines may be provided by plasma treating materials with ammonia gas as found in Holmes and Schwartz, "Amination of Ultra-high Strength Polyethylene using Ammonia Plasma", *Composites Science and Technology,* 38, 1–21 (1990). Alternatively, amines may be provided by grafting acrylamide to the substrate followed by chemical modification to introduce amine moieties by methods well known in the art, e.g., Hofmann rearrangement reaction. Polyvinylamines or polyalkylimines may also be covalently attached to polyurethane surfaces according to the method taught by U.S. Pat. No. 4,521,564 to Solomone et al. Alternatively, for example, aminosilane may be attached to the surface as set forth in U.S. Pat. No. 5,053,048 to Pinchuk, a grafted acrylamide-containing polymer may be attached by radiation grafting as set forth in U.S. Pat. No. 3,826,678 to Hoffman et al., a grafted N-(3-aminopropyl) methacrylamide-containing polymer may be attached by ceric ion grafting as set forth in U.S. Pat. No. 5,344,455 to Keogh et al.

There are a number of methods well known in the art to functionalize various moieties to monoguanidines or biguanides (diguanides). A number of these methods are discussed in a book published by John Wiley & Sons Ltd entitled *The Chemistry of Amidines and Imidates,* Vol 2, 485–526 (1991). A number of biguanides and guanidines can also be prepared from ammonium salts as described by Oxley and Short, "Amidines. Part XV. Preparation of Diguanides and Guanidines from Cyanoguanidine and Ammonium Sulphonates", *Journal of the Chemical Society,* 1252–1256 (1951). The ionic attachment of a biomolecule to a guanidino comprising surface may then be accomplished by exposing the modified biomaterial surface to a solution comprising the desired biomolecule.

Molecules which contain at least one guanidino moiety and at least one reactive moiety may be grafted to a biomaterial surface through the reactive moiety. Grafting of molecules such as monomers or polymers to biomaterial surfaces may be accomplished by a number of methods well known to those skilled in the art. For example, monomers or polymers comprising a vinyl reactive moiety may be grafted to biomaterial surfaces using various grafting methods including ceric ion initiation (CeIV), ozone exposure, corona discharge, UV irradiation or ionizing radiation ($^{60}$Co, X-rays, high energy electrons, plasma gas discharge). These grafting methods are examples of how to form free radicals on a biomaterial surface. The free radicals formed thereon initiate the grafting of the vinyl type monomers or polymers. The ionic attachment of a biomolecule to the resultant guanidino comprising surface may then be accomplished by exposing the modified biomaterial surface to a solution comprising the desired biomolecule. There are a variety of reactive moieties the guanidino comprising molecules may possess such as amino moieties, hydroxyl moieties, carboxyl moieties, aldehyde moieties, thio moieties, maleimide moieties, azide moieties, oxazidine moieties, epoxy moieties, isocyanate moieties, succinimide moieties, photochemically reactive moieties, thermochemically reactive moieties or other reactive moieties. An example of a molecule comprising a guanidino moiety and an amino moiety is (4-aminobutyl)guanidine sulfate which is also known as agmatine sulfate.

Compounds such as 1-dodecylguanidine which comprise at least one guanidino moiety and a hydrophobic region may be adsorbed from a solution onto the surface of a hydrophobic biomaterial. The hydrophobic region of the guanidino comprising compound may associate with the hydrophobic biomaterial surface through hydrophobic bonds. Adsorption of compounds comprising hydrophobic regions to hydrophobic biomaterials may be accomplished by a number of methods well known in the art. For example, amphiphilc molecules (molecules which possess a hydrophobic region and a hydrophilic region) may be used to incorporate guanidino moieties on the surface of biomaterials. Preferably, the hydrophilic region of the amphiphilc molecule would comprise the guanidino moiety.

Biomaterials that may be furnished with a net negative charge on their surface, such as polyethylene following exposure to sulfuric acid comprising potassium permanganate, may be exposed to guanidino comprising compounds, thereby reversing the surface polarity of the biomaterial surface from negative to positive. The resultant positively charged surface may then be exposed to a solution comprising the desired biomolecule. Another example of furnishing biomaterials with negatively charged surfaces is taught by U.S. Pat. No. 5,429,618 to Keogh.

Generally, biomolecules used according to this invention may be, for example, a globular protein, a structural protein, a membrane protein, a cell attachment protein, a protein, a structural peptide, a membrane peptide, a cell attachment peptide, a peptide, an anti-inflammatory agent, an antibody, an antigen, an immunoglobulin, a defense agent, a catalyst, an enzyme, a hormone, a growth factor, a neurotransmitter, a cytokine, a proteoglycan, a toxin, an antibiotic agent, an antibacterial agent, an antimicrobial agent such as penicillin, ticarcillin, carbenicillin, ampicillin, oxacillian, cefazolin, bacitracin, cephalosporin, cephalothin, cefuroxime, cefoxitin, norfloxacin, perfloxacin and sulfadiazine, a regulatory agent, a transport agent, a fibrous agent, a blood agent, a clotting agent, a platelet agent, an antithrombotic agent, an anticoagulant agent such as heparin and heparan sulfate, hyaluronic acid, a polysaccharide, a carbohydrate, a fatty acid, a nucleic acid, a DNA segment, RNA segment, a lectin, a drug, a vitamin, a ligand and a dye (which acts as a biological ligand). The biomolecules may be found in nature (naturally occurring) or may be chemically synthesized. Biomolecules which comprise at least one negatively charged moiety, such as a phosphate, a sulphate or a carboxylate, at physiological pH, may be ionically attached to a biomaterial surface by one method of the present invention. Biomolecules which comprise at least one positively charged guanidino moiety may be ionically attached to a biomaterial surface by another method of the present invention. In addition, complex biomolecule combinations of two or more biomolecules may be ionically attached to a biomaterial surface. If the biomaterial surface comprises both a negatively charged moiety and a positively charged guanidino moiety then both types of biomolecules (biomolecules comprising a negatively charged moiety and biomolecules comprising a positively charged guanidino moiety) may be attached to the biomaterial surface by both methods of the present invention.

Biomolecules may be chemically synthesized by a number of methods well known in the art. For example, a number of methods are know for synthesizing proteins or peptides from amino acids including solution (classical) synthesis methods and solid phase (e.g., SPPS) synthesis methods. Peptides of varying length may also be formed by the partial hydrolysis of very long polypeptide chains of proteins. Peptides are short chains constructed of two or more amino acids covalently joined through substituted amide linkages, termed peptide bonds. Two amino acids joined by a peptide bond forms a dipeptide. Three amino acids joined by two peptide bonds forms a tripeptide; similarly, there are tripeptides and pentapeptides. When there are many amino acids joined together, the structure is termed a polypeptide. In general, polypeptides contain less than 100 amino acid residues and proteins contain 100 or more amino acid residues. Amino acid residues comprising a negatively charged moiety include aspartic acid and glutamic acid. An amino acid residue comprising a guanidino moiety is arginine.

Some biomolecules are susceptible to conformational changes when brought into contact with a hydrophobic substrate surface. These conformational changes may lead to the exposure of internalized nonpolar groups which may lead to hydrophobic interactions between the biomolecule and the surface. These hydrophobic interactions may cause the exclusion of water molecules that normally surround the biomolecule in solution. This exclusion of water molecules between the biomolecule and the surface strengthens the hydrophobic interaction and may cause further conformational change of the biomolecule. The degree of conformational change a biomolecule experiences may or may not destroy its biological properties. Therefore, one must take into account the hydrophobic nature of the substrate surface when attaching biomolecules which are prone to hydrophobic interactions. In such cases, it is preferred to create a hydrophilic environment on the biomaterial surface, thereby preventing any unwanted hydrophobic interactions between the biomolecule and the surface which may destroy the biological properties of the biomolecule.

There are a number of surface-derivatization techniques (e.g., grafting techniques) well known in the art for creating hydrophilic substrate surfaces. For example, techniques based on ceric ion initiation, ozone exposure, corona discharge, UV irradiation and ionizing radiation ($^{60}$Co, X-rays, high energy electrons, plasma gas discharge) are known.

Substrates that may be modified according to one method of the present invention include metals such as titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers such as polyamides, polycarbonates, polyethers, polyesters, polyolefins including polyethylenes and polypropylenes, polystyrenes, polyurethanes, polyvinylchlorides, polyvinylpyrrolidones, silicone elastomers, fluoropolymers, polyacrylates, polyisoprenes, polytetrafluoroethylenes, rubber, minerals or ceramics such as hydroxapatite, human or animal protein or tissue such as bone, skin, teeth, collagen, laminin, elastin or fibrin, organic materials such as wood, cellulose or compressed carbon, and other materials such as glass, and the like. Biomaterials of the present invention made using these materials may be coated or uncoated, and derivatized or underivatized.

One method of the invention may be used to modify substrates of any shape or form including tubular, sheet, rod and articles of proper shape for use in a number of medical devices such as vascular grafts, aortic grafts, arterial, venous, or vascular tubing, vascular stents, dialysis membranes, tubing or connectors, blood oxygenator tubing or membranes, ultrafiltration membranes, intra-aortic balloons, blood bags, catheters, sutures, soft or hard tissue prostheses, synthetic prostheses, prosthetic heart valves, tissue adhesives, cardiac pacemaker leads, artificial organs, endotracheal tubes, lens for the eye such as contact or intraocular lenses, blood handling equipment, apheresis equipment, diagnostic and monitoring catheters and sensors, biosensors, dental devices, drug delivery systems, or bodily implants of any kind.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent or other publication cited herein is incorporated by reference, as if each such patent or publication were individually incorporated by reference herein.

I claim:

1. A method of forming a coating on a surface of a medical device, the coating imparting improved biocompatibility characteristics to the surface, the surface being suitable for contacting bodily tissue or fluids in or temporarily removed from a living mammalian subject, the method comprising:
   (a) providing the medical device, the medical device having a suitable biomaterial forming the surface, the biomaterial comprising a positively charged guanidino moiety;
   (b) providing a biomolecule, the biomolecule comprising a negatively charged moiety; and
   (c) combining the negatively charged moiety with the positively charged guanidino moiety to form an ionic bond, the ionic bond immobilizing the biomolecule on the surface, the immobilized biomolecule forming the coating.

2. The method of claim 1, wherein the medical device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

3. The method of claim 1, wherein the negatively charged moiety is selected from the group consisting of a phosphate, a sulphate and a carboxylate.

4. The method of claim 1, wherein the guanidino moiety is an arginine amino acid.

5. The method of claim 1, wherein the biomolecule is a naturally occurring biomolecule.

6. The method of claim 1, wherein the biomolecule is a chemically synthesized biomolecule.

7. The method of claim 1, wherein the biomolecule is selected from the group consisting of a globular protein, a cell attachment protein, a protein, a cell attachment peptide, a peptide, an anti-inflammatory agent, an antibody, an antigen, an immunoglobulin, an enzyme, a hormone, a growth factor, a neurotransmitter, a cytokine, a proteoglycan, a toxin, an antibiotic agent, an antibacterial agent, an antimicrobial agent, an antithrombotic agent, a polysaccharide, a carbohydrate, a fatty acid, a nucleic acid, a DNA segment, RNA segment, a lectin, a drug, a vitamin and a ligand.

8. The method of claim 1, wherein at least a portion of the surface forms at least one of a tube, a rod, a membrane, a balloon, a bag and a sheet.

9. The method of claim 1, wherein the medical device comprises at least one of a biocompatible material selected from the group consisting of metal, titanium, titanium alloys, tin-nickel alloys, shape memory alloys, aluminum oxide, platinum, platinum alloys, stainless steel, MP35N stainless steel, elgiloy, stellite, pyrolytic carbon, silver carbon, glassy carbon, polymer, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin, elastin, fibrin, wood, cellulose, compressed carbon and glass.

10. A method of forming a coating on a surface of a medical device, the coating imparting improved biocompatibility characteristics to the surface, the surface being suitable for contacting bodily tissue or fluids in or temporarily removed from a living mammalian subject, the method comprising:
 (a) providing the medical device, the device having a suitable biomaterial forming the surface, the biomaterial comprising an amine moiety;
 (b) combining the amine moiety with a guanidino forming agent to form a positively charged guanidino moiety on the surface;
 (c) providing a biomolecule, the biomolecule comprising a negatively charged moiety; and
 (d) combining the negatively charged moiety with the positively charged guanidino moiety to form an ionic bond, the ionic bond immobilizing the biomolecule on the surface, the immobilized biomolecule forming the coating.

11. The method of claim 10, wherein the device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

12. The method of claim 10, wherein the guanidino forming agent is selected from the group consisting of S-ethylthiouronium bromide, S-ethylthiouronium chloride, O-methylisourea, O-methylisouronium sulfate, O-methylisourea hydrogen sulfate, S-methylisothiourea, 2-methyl-1-nitroisourea, aminoiminomethanesulfonic acid, cyanamide, cyanoguanide, dicyandiamide, 3,5-dimethyl-1-guanylpyrazole nitrate and 3,5-dimethyl pyrazole.

13. The method of claim 10, wherein the negatively charged moiety is selected from the group consisting of a phosphate, a sulphate and a carboxylate.

14. The method of claim 10, wherein the guanidino moiety is an arginine amino acid.

15. The method of claim 10, wherein the biomolecule is a naturally occurring biomolecule.

16. The method of claim 10, wherein the biomolecule is a chemically synthesized biomolecule.

17. The method of claim 10, wherein the biomolecule is selected from the group consisting of a globular protein, a cell attachment protein, a protein, a cell attachment peptide, a peptide, an anti-inflammatory agent, an antibody, an antigen, an immunoglobulin, an enzyme, a hormone, a growth factor, a neurotransmitter, a cytokine, a proteoglycan, a toxin, an antibiotic agent, an antibacterial agent, an antimicrobial agent, an antithrombotic agent, a polysaccharide, a carbohydrate, a fatty acid, a nucleic acid, a DNA segment, RNA segment, a lectin, a drug, a vitamin and a ligand.

18. The method of claim 10, wherein at least a portion of the surface forms at least one of a tube, a rod, a membrane, a balloon, a bag and a sheet.

19. The method of claim 10, wherein the medical device comprises at least one of a biocompatible material selected from the group consisting of metal, titanium, titanium alloys, tin-nickel alloys, shape memory alloys, aluminum oxide, platinum, platinum alloys, stainless steel, MP35N stainless steel, elgiloy, stellite, pyrolytic carbon, silver carbon, glassy carbon, polymer, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin; elastin, fibrin, wood, cellulose, compressed carbon and glass.

20. A method of forming a coating on a surface of a medical device, the coating imparting improved biocompatibility characteristics to the surface, the surface being suitable for contacting bodily tissue or fluids in or temporarily removed from a living mammalian subject, the method comprising:
 (a) providing the medical device, the device having a suitable biomaterial forming the surface, the biomaterial comprising a negatively charged moiety;
 (b) providing a biomolecule, the biomolecule comprising an amine moiety;
 (c) combining the amine moiety with a guanidino forming agent to form a positively charged guanidino moiety; and (d) combining the positively charged guanidino moiety with the negatively charged moiety to form an ionic bond, the ionic bond immobilizing the biomolecule on the surface, the immobilized biomolecule forming the coating.

21. The method of claim 20, wherein the device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

22. The method of claim 20, wherein the guanidino forming agent is selected from the group consisting of S-ethylthiouronium bromide, S-ethylthiouronium chloride, O-methylisourea, O-methylisouronium sulfate, O-methylisourea hydrogen sulfate, S-methylisothiourea, 2-methyl-1-nitroisourea, aminoiminomethanesulfonic acid, cyanamide, cyanoguanide, dicyandiamide, 3,5-dimethyl-1-guanylpyrazole nitrate and 3,5-dimethyl pyrazole.

23. The method of claim 20, wherein the negatively charged moiety is selected from the group consisting of a phosphate, a sulphate and a carboxylate.

24. The method of claim 20, wherein the guanidino moiety is an arginine amino acid.

25. The method of claim 20, wherein the biomolecule is a naturally occurring biomolecule.

26. The method of claim 20, wherein the biomolecule is a chemically synthesized biomolecule.

27. The method of claim 20, wherein the biomolecule is selected from the group consisting of a globular protein, a cell attachment protein, a protein, a cell attachment peptide, a peptide, an anti-inflammatory agent, an antibody, an antigen, an immunoglobulin, an enzyme, a hormone, a growth factor, a neurotransmitter, a cytokine, a proteoglycan, a toxin, an antibiotic agent, an antibacterial agent, an antimicrobial agent, an antithrombotic agent, a polysaccharide, a carbohydrate, a fatty acid, a nucleic acid, a DNA segment, RNA segment, a lectin, a drug, a vitamin and a ligand.

28. The method of claim 20, wherein at least a portion of the surface forms at least one of a tube, a rod, a membrane, a balloon, a bag and a sheet.

29. The method of claim 20, wherein the medical device comprises at least one of a biocompatible material selected from the group consisting of metal, titanium, titanium alloys, tin-nickel alloys, shape memory alloys, aluminum oxide, platinum, platinum alloys, stainless steel, MP35N stainless steel, elgiloy, stellite, pyrolytic carbon, silver carbon, glassy carbon, polymer, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin, elastin, fibrin, wood, cellulose, compressed carbon and glass.

\* \* \* \* \*